United States Patent [19]
Scholey et al.

[11] Patent Number: 5,954,229
[45] Date of Patent: Sep. 21, 1999

[54] WALL MOUNTED EARPLUG DISPENSER

[75] Inventors: Michael Forbes Scholey, Pacoima; Chick Ngai, Torrance; Norman John Smith, Los Angeles, all of Calif.

[73] Assignee: Moldex-Metric, Inc, Culver City, Calif.

[21] Appl. No.: 08/951,963

[22] Filed: Oct. 16, 1997

[51] Int. Cl.[6] .................................................. A24F 15/04
[52] U.S. Cl. ............................................ 221/186; 221/265
[58] Field of Search .................................... 221/186, 188, 221/265, 277, 282, 285, 263, 155, 197

[56] References Cited

U.S. PATENT DOCUMENTS

| | | | |
|---|---|---|---|
| 3,330,442 | 7/1967 | O'Connor | 221/265 |
| 5,443,179 | 8/1995 | Palmer et al. | 221/265 |

*Primary Examiner*—Kenneth W. Noland
*Attorney, Agent, or Firm*—Charles H Schwartz

[57] ABSTRACT

An earplug dispenser for manual operation by a user includes a bottle member to receive a plurality of earplugs. A dispensing mechanism is located at an open end of the bottle member so that when the bottle member is turned upside down, the dispensing mechanism projects downward and the earplugs fall by gravity to the dispensing mechanism. The dispensing mechanism includes an impeller member having a plurality of impeller openings to have individual earplugs located within the impeller openings by gravity and additionally includes a knob member projecting downward from the impeller so that the rotation of the knob provides for rotation of the impeller and any individual earplugs captured in the impeller openings. The dispensing mechanism also includes a separate dispensing opening located adjacent the knob member and in line with the impeller openings so that as the knob is rotated progressive ones of the impeller openings containing individual earplugs are directed above the dispensing openings to allow the earplugs to fall out of the dispensing mechanism into the hand of the user. A holder member receives the bottle and dispensing mechanism and supports the bottle and dispensing mechanism in a position to have the knob and dispensing mechanism located so that a user can rotate the knob and at the same time receive the individual dispensed earplugs into the hand of the user.

18 Claims, 4 Drawing Sheets

5,954,229

WALL MOUNTED EARPLUG DISPENSER

BACKGROUND OF INVENTION

The present invention relates to a wall mounted earplug dispenser and specifically to a transparent plastic bottle for storing earplugs and with the bottle including a built-in dispenser mechanism. The entire bottle and dispenser mechanism is detachably mounted on a wall bracket to allow for a user to easily dispense earplugs when desired.

In the prior art, wall mounted earplug dispensers have generally been quite complicated in structure. Reference is made to wall mounted earplug dispensers as shown in the following U.S. Pat. Nos. 5,285,925; 5,372,278; 5,280,845 and 5,322,185.

As can been seen in the above referenced patents, the prior art structures have been quite complex and include separate permanent mechanisms for receiving earplugs and mechanical crank mechanisms to dispense the earplugs. These prior art devices have been quite expensive because of their complexity and such expense has limited their use in industry. In addition, these prior art earplugs have had problems of the earplugs jamming the mechanism when being dispensed and these prior art structures have included special adaptations to clear jams. It would be desirable to provide for the dispensing of the earplugs without complicated structures that can jam.

SUMMARY OF THE INVENTION

The present invention includes a simple structure for dispensing earplugs. The structure includes a wall mounted holder which is molded plastic and is relatively inexpensive. The holder is formed of two pieces which can be snapped together and simply mounted to the wall or positioned on a table. In addition, the earplugs are dispensed from a bottle member made of inexpensive plastic so that the bottle member can serve both as the shipping container and supply unit for the earplugs and the bottle can be disposable after use. In addition, a dispensing mechanism is mounted at the end of the bottle and again the dispensing mechanism is made of relatively inexpensive plastic material. The whole unit, including the bottle and the dispensing mechanism, can be disposable so that the entire structure may be disposed of after all of the earplugs are dispensed. The bottle member includes portions which interlock to the wall holder so that the bottle member may be slid into position and after all of the earplugs are dispensed the bottle member may be slid up and out and be replaced by a new bottle member.

The dispensing mechanism of the present invention includes an impeller located at the bottom of the bottle. Once the bottle is installed in the wall member, the impeller funnels earplugs into a series of openings in the impeller. The earplugs are carried along to a dispensing opening at the bottom of the bottle as the impeller is rotated by an integral knob member. The earplugs therefore lie on top of the impeller and are moved along by the impeller to the impeller openings and ultimately to the dispensing position. A simple rotation of the knob member by the user of the earplugs provide for the earplugs falling downward into the hand of the user as the impeller is rotated.

One of the problems with the prior art is that the earplugs, because they are soft and compliant, tend to jam the dispensing mechanism as the earplugs are rotated into position for dispensing. The prior art has tried to maintain small tolerances so that the earplugs cannot jam. In practice, jams occur and the prior art devices typically include openings to the outside of the dispenser to provide for the unjamming of the dispenser using an implement from an outside position. The present invention eliminates the problem of jamming by actually having a sufficient spacing between the impeller and a bottom wall of the dispenser so that the earplugs can be rolled without jamming from one position to another as the impeller is rotated. In this way the earplugs cannot jam but rather are carried along either in the impeller openings or recesses in the impeller. The earplugs are simply dispensed without any problem of jamming of the earplugs in the dispensing mechanism.

DETAILED DESCRIPTION OF THE PREFERRED EMBODIMENT

Figure 1:
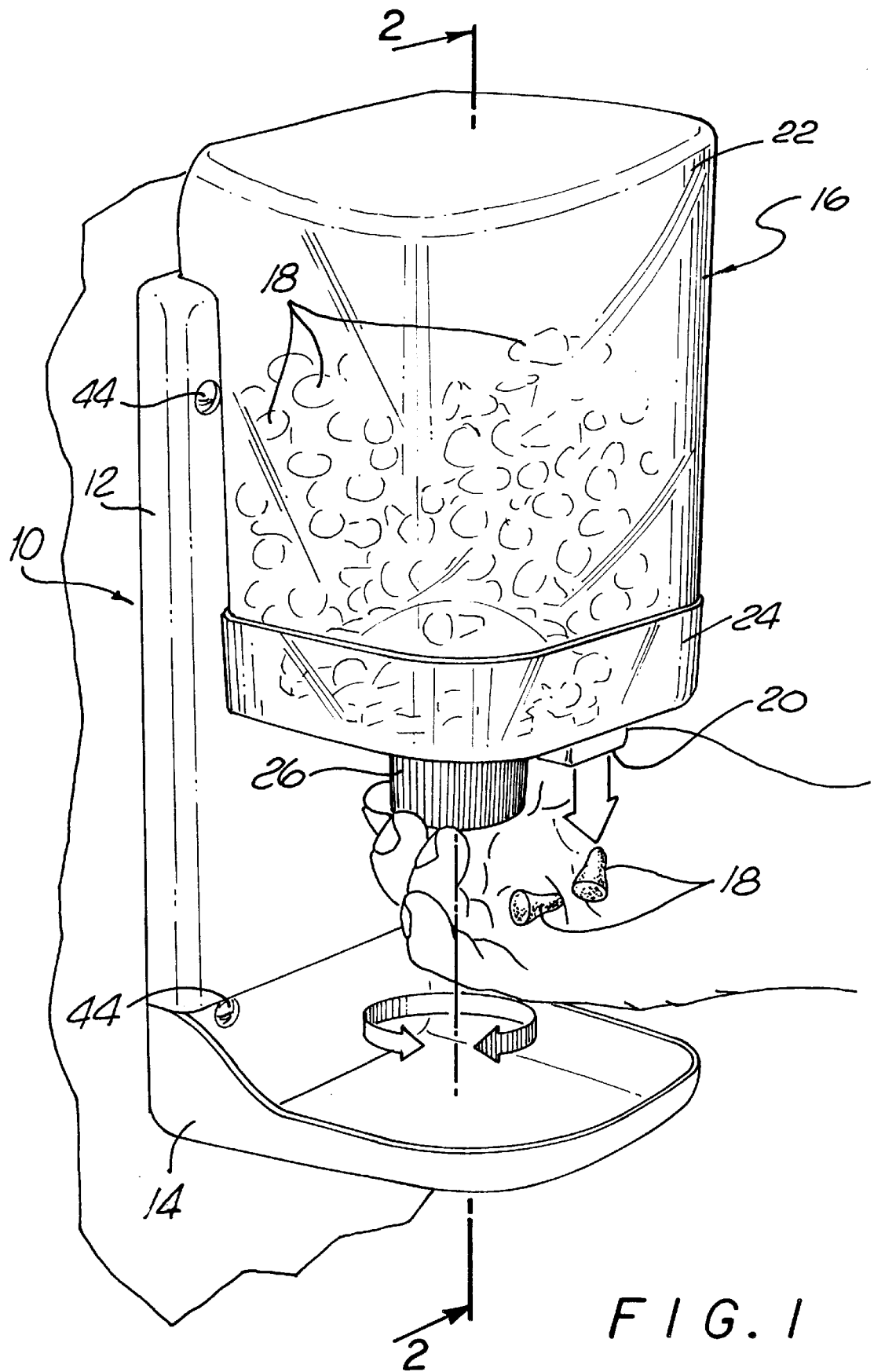
FIG. 1 is a front perspective view of the wall mounted earplug dispensing assembly of the present invention.

As shown in FIG. 1, a wall mounted earplug dispenser includes a wall mount 10 formed of two component portions 12 and 14 which serves as a bottle holder. A transparent plastic dispensing bottle 16 interlocks with wall mount portion 12 to have earplugs 18 dispensed from the bottle 16 through a dispenser opening 20 into the hand of user. Any excess earplugs will fall into the holder portion 14 which serves as a bottom receptacle for any plugs that are not captured by the hand of the user.

The bottle 16 includes a large container portion 22 to receive the earplugs 18 and a cap member 24 supporting a dispensing mechanism operated by a rotateable knob 26. The knob 26 is actuated by the hand of the user to provide for the dispensing of the earplugs from the opening 20. The knob 26 when rotated operates an internal impeller 28, not shown in FIG. 1 since it is obscured by the earplugs lying on the impeller. The impeller may be seen in FIGS. 2 through 6 which details the unique operation of the present invention to provide for the dispensing of the earplugs 18 from the opening 20.

Figure 2:
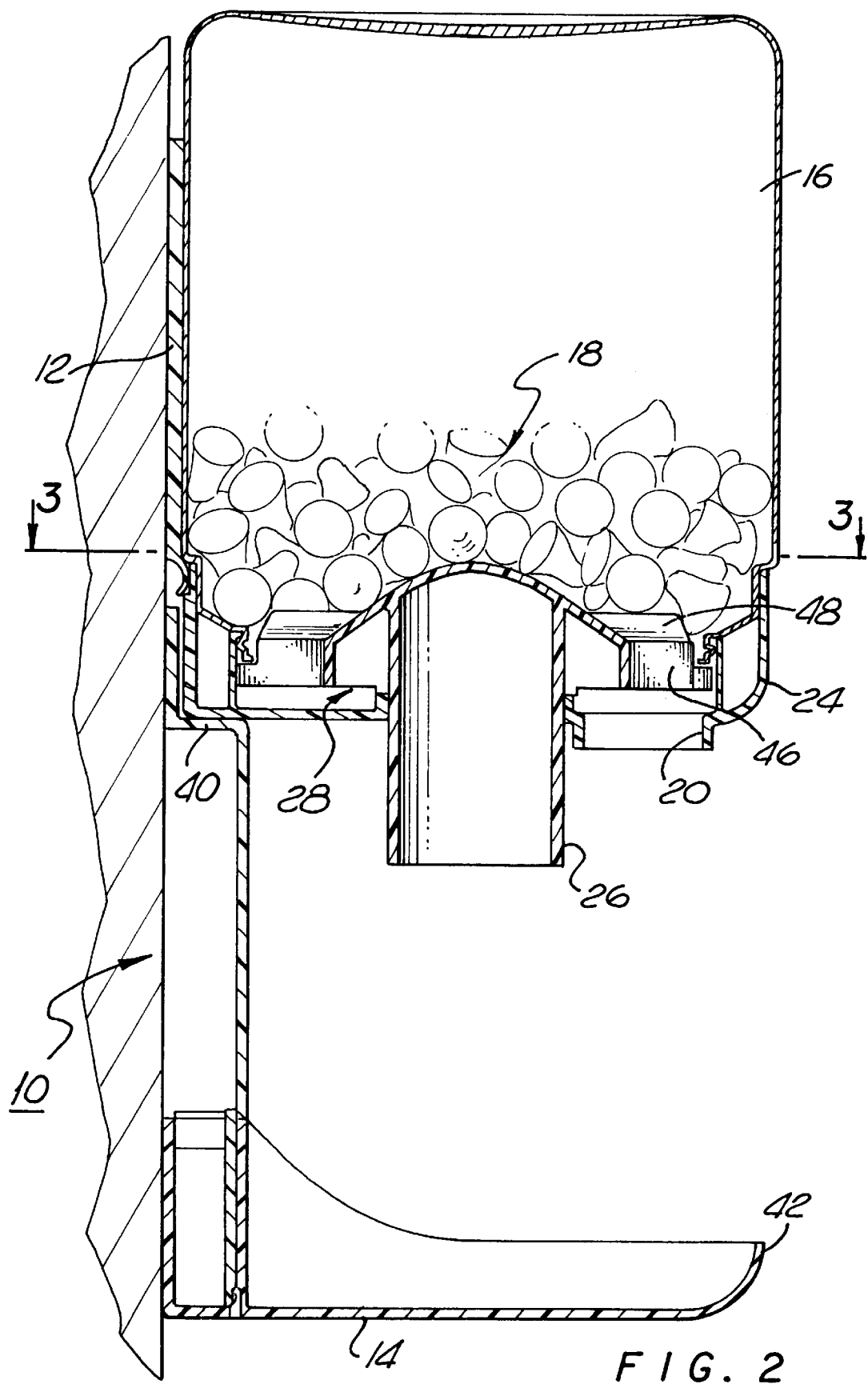
FIG. 2 is a cross sectional view taken along lines 2—2 of FIG. 1.
Figure 3:
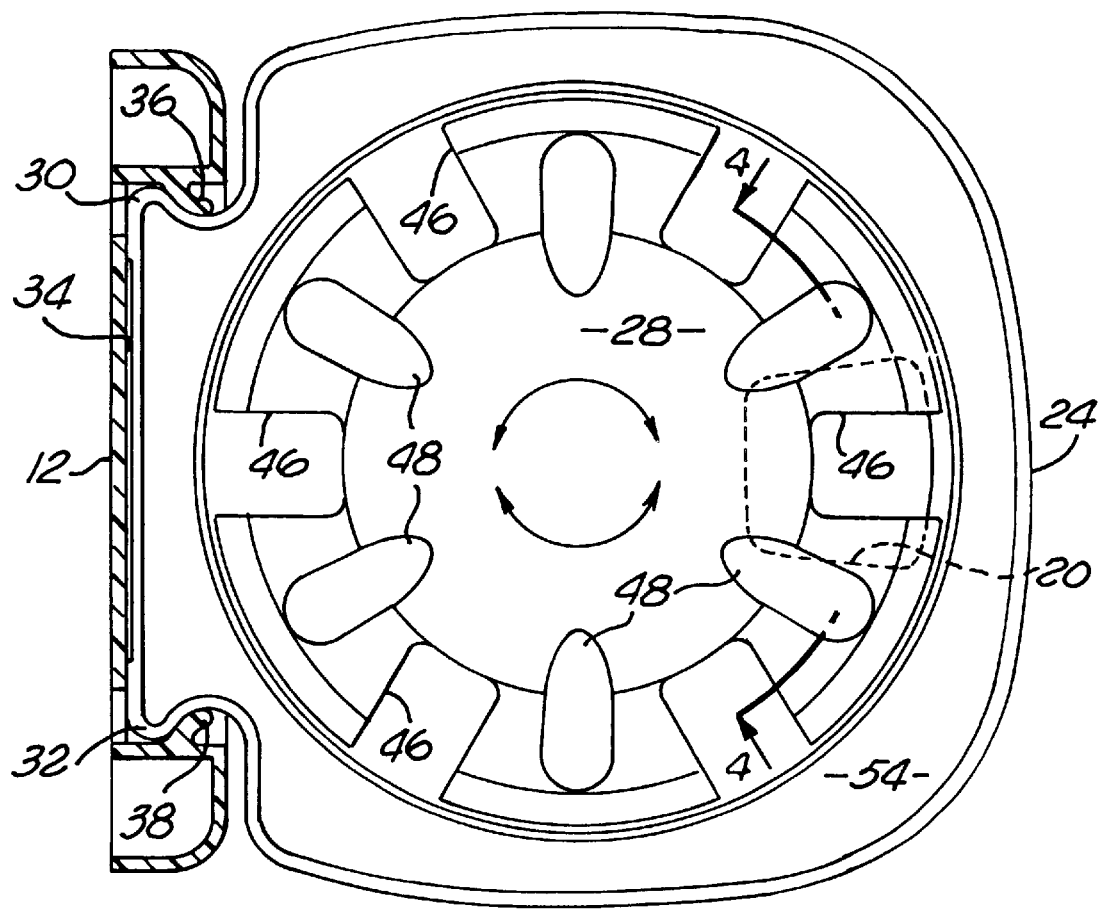
FIG. 3 is a cross sectional view taken along lines 3—3 of FIG. 2.

As shown in FIGS. 2 and 3 the bottle 16 is mounted to the wall mount portion 12 using integral flanges 30 and 32 formed at the back of the bottle 16. The flanges 30 and 32 slide into a recess 34 formed in the wall mount portion 12 and with small wings 36 and 38 cooperating with the flange portions 30 and 32 of the bottle to lock the bottle 16 in position against the back surface of the wall mount portion 12. As can be seen in FIG. 2, when the bottle is in position against the back wall of the wall mount section 12, the bottle can only go as low as a position formed by a stop surface 40 formed in the wall mount portion 12.

As indicated above, the wall mount 10 also includes a lower portion 14 and as can be seen in FIG. 2 the wall mount portions 12 and 14 interlock so that the wall mount portion 14 projects from the wall and acts as a receiver for any earplugs which may drop out of the hand of the user. The wall mount portion 14 is formed as a shallow bowl having a lip 42 which projects upwardly all around the wall mount portion 14. As shown in FIG. 1, screws 44 pass through openings in the wall mount and lock the wall mount 10 to the wall.

The bottle 16 includes the cap 24 which fits over the end of the bottle to close off and seal the contents of the bottle. Except for the opening 20, which allows the earplugs to fall out into the hand of the user, the cap 24 seals in the earplugs 18 and may be permanently attached to the bottle 16 so that the entire bottle and its contents of earplugs form one disposable unit. Alternately the cap 24 may merely be friction fit onto the end of the bottle 16. A temporary cap may be used to initially seal the bottle, and then when the earplugs are to be dispensed, this temporary cap can be removed and the cap 24 placed on the bottle 16. The dispensing unit is then turned upside down and inserted into the wall mount as shown in FIG. 1.

The cap is constructed to receive and hold in position the impeller 28. The impeller moves the earplugs from a storage position within the bottle to a plurality of impeller openings 46 and ultimately to the dispensing opening 20 to be received in the hand of the user as the impeller is rotated by the knob 26. The structure of the impeller and the relationship of the impeller 28 to the cap 24 can be seen in detail in FIGS. 2 through 6.

Figure 4:
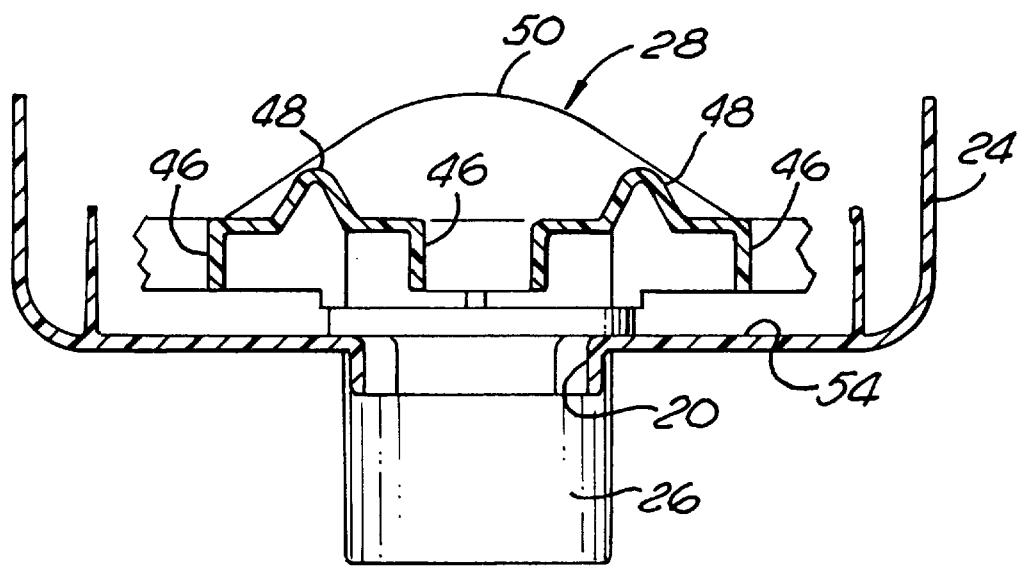
FIG. 4 is a cross sectional view taken along lines 4—4 of FIG. 3.
Figure 5:
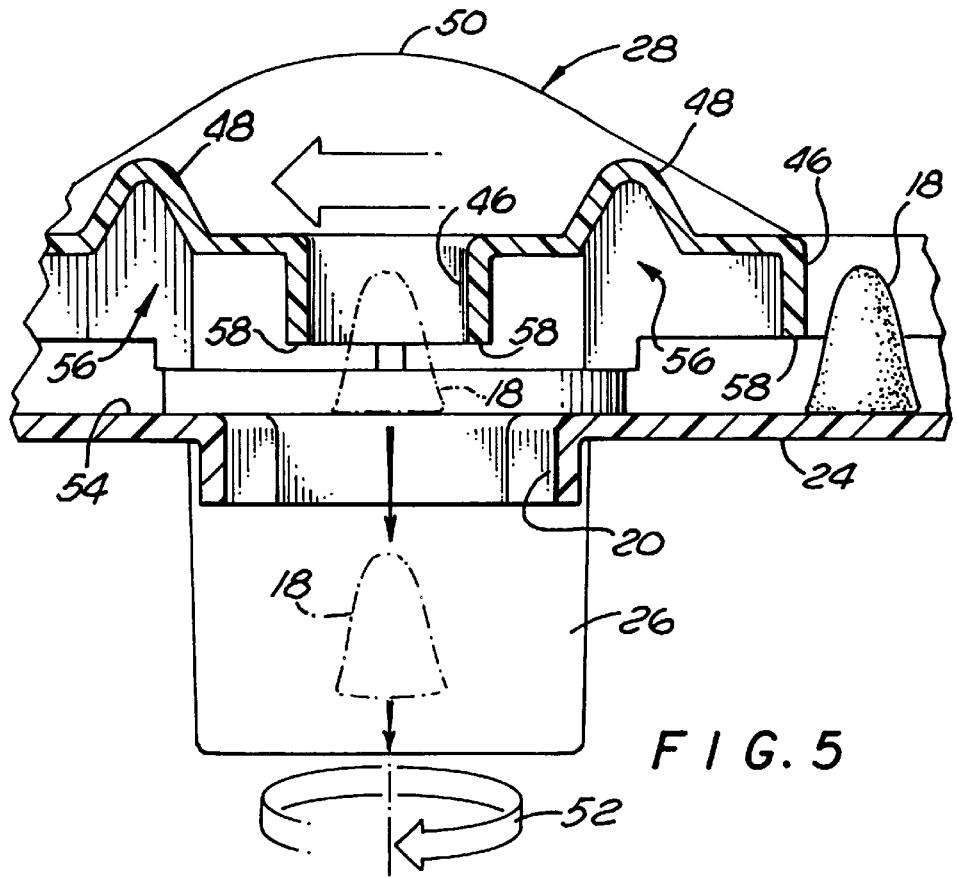
FIG. 5 is an enlarged cross sectional view of a portion of FIG. 4 and showing earplugs being moved along to a dispensing position.
Figure 6:
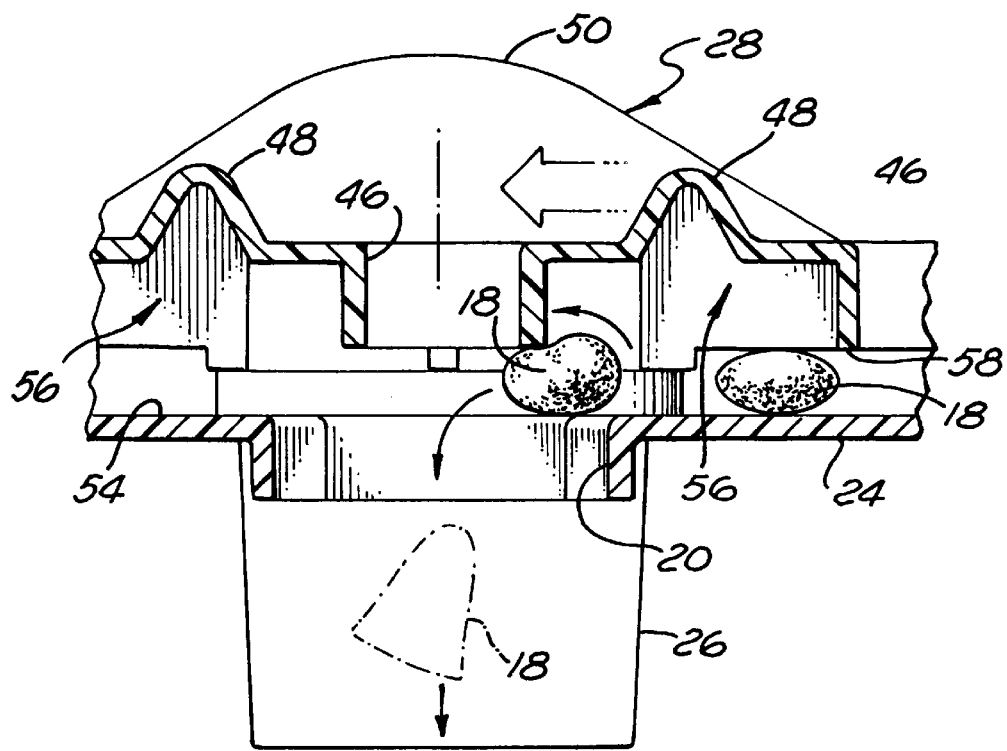
FIG. 6 is a similar cross sectional view of a portion of FIG. 4 and showing how an earplug maybe rolled out of a dispensing position to a recess so as to prevent any jamming and yet dispense the earplugs from the dispenser.

FIG. 3 illustrates a top view of the impeller 28 and as can be seen, the impeller includes the plurality of openings 46 spaced equally around the circumference of the impeller and a plurality of upstanding ridges 48 also spaced equally around the circumference of the impeller. As shown in FIGS. 4 through 6 the central portion of the impeller is formed as a hump 50 to gently guide the earplugs down between the ridges 48 towards the openings 46. The ridges 48 also tend to stir up the earplugs 18 to further enhance the earplugs moving down the slope of the hump 50 between the upstanding ridges 48 to the openings 46. All this is accomplished as the impeller is turned either clockwise or counterclockwise by the user using the knob 26.

The rotation of the knob 26 provides for the dispensing of individual earplugs through the opening 20 each time one of the impeller openings 46 is aligned with the dispensing opening 20 or each time one of the earplugs is pulled along to a position above the dispensing opening 20. The dispensing of the earplugs can be accomplished in either one of two ways as shown in FIGS. 5 and 6.

The normal operation of the earplug dispenser of the present invention is shown in FIG. 5 where as earplug 18 is guided down the slope of the central hump portion 50 of the impeller 28 and between the upstanding ridges 48 and is received in an opening 46. As the impeller is rotated as shown by the arrow the 52, the opening 46 is brought to the position shown by the dotted line for the earplug 18 so that the earplug can fall down from the impeller opening 46 and through the dispensing opening 20 to the hand of the user. The rotation of the impeller occurs by the user turning the knob 26.

Unfortunately, in order for the impeller 28 to rotate freely relative to an inside bottom wall 54 of the cap member 24, there has to be some spacing between the bottom of the impeller and the wall 54. If this spacing is close, as with prior art devices, then the earplugs which are very pliable could be captured in this close spacing and jam the impeller from rotating and damage the earplugs. In the prior art, impellers are located very close to a bottom wall and jamming occurs. In the prior art, access is provided to an outside position so a tool can be inserted to dislodge the jammed earplug.

In the present invention, as can be seen in FIGS. 5 and 6, the impeller 28 is made to be hollow in the positions between the openings 46 as shown by the hollow areas 56. In addition, the bottom surface 58 of the impeller in the areas that form the openings 46 is spaced a distance from the wall 54 so that the earplug 18 can roll down into the hollow areas 56 when contacted by the bottom surface 58. As shown in FIG. 6 an earplug 18 has been turned on its side and has been contacted by the bottom surface 58 and compressed to the shape shown in FIG. 6 and pulled into the hollow area 56. As the impeller is rotated, the earplug 18 is captured within the hollow area 56 and is pulled over the dispensing opening 20 and dispensed as shown by earplug 18 in dotted line in FIG. 6.

The space in between the bottom surface 58 of the impeller 28 and the top surface of the wall member 54 is generally at least sufficient so that the earplug when rolled down will not be damaged and can recover to its original shape. Also the space is smaller than the diameter of the earplug so that the earplug will normally be rotated along the wall member 54 while captured in the impeller openings 46 to be dispensed through the dispensing opening 20 as shown in FIG. 5.

The spacing therefore may be considered to be less than the diameter of the earplug 18 but normally no less than approximately 25% to 30% of the greatest diameter of the earplug. Since the earplugs are typically of the type that can be rolled down to a fraction of their diameter for insertion into the ear canal, even using a spacing smaller than 25% to 30% of the diameter of the earplug would work but could provide for more difficulty in rotating the impeller using the knob 26 and could damage the earplugs. A greater spacing such as 35% to 65% of the diameter of the earplug allows the impeller to be rotated smoothly and with earplugs rolling into the openings 46. As a specific example, the spacing is approximately 50% of the diameter of the earplugs. In any of the earplugs do become captured in the space between the bottom surface 58 and the wall 54 these earplugs would be smoothly rolled down into the hollow 56 to be dispensed through the opening 20 as shown in FIG. 6.

The use of the structure of the present invention completely eliminates the necessity of having any additional access to the interior of the dispenser and liminates the need for any tools to dislodge jammed earplugs.

The present intention therefore is directed to a simple earplug dispenser unit which is preferably wall-mounted but could also be table mounted and with the receptacle for the earplugs being a transparent bottle member which may itself be completely disposable or may have a disposable portion and a reusable portion. The bottle member is inserted into the mounting unit to allow for simple and easy dispensing of earplugs to a user by merely rotating a knob and allowing earplugs to drop into the hand of the user.

The design of the earplug dispenser of the present invention is very inexpensive so that the bottle member may be completely disposable including the dispensing structure. Each time a bottle is inserted into the mount, a fresh dispensing member is provided which would tend to eliminate any problems of wear or other failures that can occur over time as a structure is being used on a regular basis. The present invention provides for a very simple structure and a structure which eliminates the problem of jamming by providing for a space between the impeller and the bottom wall where jamming can occur so that instead of jamming an earplug is gently rolled into a hollow recess for dispensing through the normal opening in the bottom wall.

Although the invention has been described with reference to a particular embodiment it should be appreciated that other adaptations and modifications may be made and the invention is only to be limited by the appended claims.

We claim:

1. A wall mounted earplug dispenser for manual operation by a user, including:
   a wall mount for attachment to a wall to receive and support an earplug dispenser and with the wall mount including a back portion for attachment to the wall and a portion projecting outwardly from the wall to capture any earplugs dispensed from the earplug dispenser,
   a bottle member detachably received and supported by the wall mount and with the wall mount and the bottle member including reciprocal structures to allow the bottle member to be slid into the wall mount to be received and supported in a position so that the bottle member extends downwardly towards the portion of the wall mount which projects away from the wall and with the bottle member containing a plurality of earplugs,
   the bottle member additionally including a dispensing mechanism, mounted at the bottom of the bottle member, and with the dispensing mechanism including a dispensing opening to allow earplugs contained in the bottle to fall downward towards the portion of the wall mount that projects away from the wall and into the hand of the user,
   the dispensing mechanism including a rotatable impeller with a plurality of impeller openings to receive individual earplugs in each impeller opening and with rotation of the impeller providing for each impeller opening in turn to be rotated towards the dispensing opening to have the individual earplugs drop through the dispensing opening into the hand of the user, and
   the dispensing mechanism including a knob projecting downward from the dispensing mechanism and attached to the impeller so that the user of the earplug dispenser can rotate the knob to rotate the impeller to have the individual earplugs fall into the impeller openings and to have the impeller openings in turn positioned over the dispensing opening located above the hand of the user.

2. The wall mounted earplug dispenser of claim 1 wherein the wall mount portion's are formed of separate members which snap together.

3. The wall; mounted earplug dispenser of claim 1 wherein the bottle member is made of transparent material so that the quantity of earplugs is visible.

4. The wall mounted earplug dispenser of claim 1 wherein the reciprocal structures are a recess and complimentary flanges in the wall mount and bottle member.

5. The wall mounted earplug dispenser of claim 1 wherein the impeller includes a central raised portion forming a hump to guide the earplugs to the impeller openings.

6. The wall mounted earplug dispenser of claim 1 wherein the impeller includes a plurality of upstanding ridges individually located intermediate the impeller openings to guide the earplugs to the impeller openings.

7. The wall mounted earplugs dispenser of claim 1 wherein the dispensing mechanism includes a bottom wall and with the dispensing openings located in the bottom wall and with the impeller spaced from the bottom wall a distance less than the diameter of an individual earplug but greater than 25% of the diameter of an earplug to prevent jamming of an earplug during rotation of the impeller.

8. The wall mounted earplug dispenser of claim 7 wherein the spacing distance is approximately 50% of the diameter of an earplug.

9. The wall mounted earplug dispenser of claim 7 wherein the impeller includes recesses located intermediate the impeller opening to receive any earplugs rolling through the spacing between the impeller and the bottom wall of the dispensing mechanism.

10. An earplug dispenser for manual operation by a user including
    a bottle member to receive a plurality of earplugs,
    a dispensing mechanism located at an open end of the bottle member so that when the bottle member is turned upside down, the dispensing mechanism projects downward and the earplugs fall by gravity to the dispensing mechanism
    the dispensing mechanism including an impeller member having a plurality of impeller openings to have individual earplugs located within the impeller openings by gravity and additionally including a knob member projecting downward from the impeller so that the rotation of the knob provides for rotation of the impeller and any individual earplugs captured in the impeller openings,
    the dispensing mechanism also including a separate dispensing opening located adjacent the knob member and in line with the impeller openings so that as the knob is rotated progressive ones of the impeller openings containing individual earplugs are directed above the dispensing openings to allow the earplugs to fall out of the dispensing mechanism into the hand of the user, and
    a holder member for receiving the bottle and dispensing mechanism and for supporting the bottle and dispensing mechanism in a position to have the knob and dispensing mechanism located so that a user can rotate the knob and at the same time receive the individual dispensed earplugs into the hand of the user.

11. The earplug dispenser of claim 10 wherein the holder is formed of separate members which snap together.

12. The earplug dispenser of claim 10 wherein the bottle member is made of transparent material so that the quantity of earplugs is visible.

13. The earplug dispenser of claim 10 wherein the bottle is received by the holder using a recess and complimentary flanges in the holder and bottle member.

14. The earplug dispenser of claim 10 wherein the impeller includes a control raised portion forming a hump to guide the earplugs to the impeller openings.

15. The earplug dispenser of claim 10 wherein the impeller includes a plurality of upstanding ridges individually located intermediate the impeller openings to guide the earplugs to the impeller openings.

16. The earplug dispenser of claim 10 wherein the dispensing mechanism includes a bottom wall and with the dispensing openings located in the bottom wall and with the impeller spaced from the bottom wall a distance less than the diameter of an individual earplug but greater than 25% of the diameter of an earplug to prevent jamming of an earplug during rotation of the impeller.

17. The earplug dispenser of claim 16 wherein the spacing distance is approximately 50% of the diameter of the earplug.

18. The earplug dispenser of claim 16 wherein the impeller includes recesses located intermediate the impeller opening to receive any earplugs rolling through the spacing between the impeller and the bottom wall of the dispensing mechanism.

* * * * *